(12) United States Patent
Schmitthaeusler

(10) Patent No.: US 7,771,725 B2
(45) Date of Patent: Aug. 10, 2010

(54) MEDICINAL CONCENTRATE OF ARBOVIRUS SPECIFIC IMMUNOGLOBULINS AND F(AB)'2 AND/OR FAB FRAGMENTS

(75) Inventor: Roland Schmitthaeusler, Montigny le Bretonneux (FR)

(73) Assignee: Laboratoire Fancais du Fractionnement et des Biotechnologies, Les Ulis (FR)

( * ) Notice: Subject to any disclaimer, the term of this patent is extended or adjusted under 35 U.S.C. 154(b) by 6 days.

(21) Appl. No.: 11/912,444

(22) PCT Filed: Apr. 2, 2007

(86) PCT No.: PCT/FR2007/000560

§ 371 (c)(1),
(2), (4) Date: May 14, 2008

(87) PCT Pub. No.: WO2007/118986

PCT Pub. Date: Oct. 25, 2007

(65) Prior Publication Data

US 2009/0041780 A1 Feb. 12, 2009

(30) Foreign Application Priority Data

Mar. 31, 2006 (FR) .................................. 06 02803

(51) Int. Cl.
*A61K 39/42* (2006.01)
*C12P 21/06* (2006.01)
*C07K 16/10* (2006.01)

(52) U.S. Cl. .................. 424/159.1; 530/389.4; 530/407; 530/418; 530/417; 530/412; 435/68.1

(58) Field of Classification Search ........................ None
See application file for complete search history.

(56) References Cited

U.S. PATENT DOCUMENTS

2005/0182080 A1  8/2005 Chamberlain et al.

FOREIGN PATENT DOCUMENTS

EP          1385886        11/2002
WO      WO2004091656       10/2004

OTHER PUBLICATIONS

Cruse et al. "Illustrated Dictionary of Immunology." CRC press, Boca Raton, FL, 1995, p. 107.*
Shimoni et al. Emerging Infectious Diseases 7(4):759 (2001).*
Ben-Nathan et al. The Journal of Infectious Diseases 188:5-12 (2003).*
Agrawal et al. The Journal of Infectious Diseases 188:1-4 (2003).*
Kreil et al. Journal of Virology 71: 2921-2927 (1997).*
Van Furth et al. The Journal of Infectious Diseases 149:511-517 (1984).*
Boere et al. Journal of Virology 54:546-551 (1985).*
Erlich et al. Antimicrobial Agents and Chemotherapy 31: 1006-1009 (1987).*
Steele et al. Journal of Clinical Microbiology 27:640-643 (1989).*
Thullier et al (Journal of Biotechnology 69:183-190, 1999).*
Dreffier, et al., "Immunoprophylaxie des infections respiratoires," Medicine/Sciences 2004, vol. 20, pp. 999-1003.
Kunishige M, et al., "Preferential gray matter involvement in dengue myelitis," Neurology, Nov. 2004, vol. 63, No. 10, pp. 1980-1981.
Gaidamovitch et al. 1973 (Database EMBASE).
Giovarelli et al. "Effect of Anti-u-Chain Specific Immunosuppression on Chikungunya Virus Encephalitis of Mice," Infection and Immunity, vol. 16, No. 3, Jun. 1977, pp. 849-852.
Pialoux et al., "Chikungunya virus invection: review through an epidemic," Medecine et maladies infectieuses 36 (2006) pp. 253-263.
Edelman R. et al., "Phase II safety and immunogenecity study of live chikungunya virus vaccine," Jun. 2000, Am. J. Trop. Med. Hyg., 62:681-5.
Ohara et al., "Prophylactic Efficacy of mmune erum Globulin against Hepatitis A," Jpn J. Exp. Med. 1986, 56(5):229-33.
Conrad Me et al., "Prevention of Endemic Icteric Viral Hepatitis by Administration of Immune Serum Gamma Globulin," J. Infect. Dis. 1987, 156(1):56-63.
Oncley et al., "The Separation of the Antibodies, Isoagglutinins, Prothrmbin, Plasminogen and B1-Lipoprotein into Subfractions of Human Plasma," 1949 J. Am. Chem. Soc. 71:541.
Van de Water et al., "Rapid in vitro micro-cytotoxicity tests for the detection and quantitation of neutralizing antibodies to both viruses and toxins," Journal of Immunological methods 166(1993): 157-164.
Steinbuch M., "The isolation of IgG From Mammalian Sera with the Aid of Caprylic Actid," Archiv. Biochem. Biophys., 134:279-284 (1969).
Briolant et al., "In vitro inhibition of Chikungunya and Semliki Forest viruses replication by antiviral compounds: synergistic effect of enterferon-$\alpha$ and ribavirin combination," 2004.
Igarashi et al. (Passive immunization of mice with rabbit antisera against Chikungunya virus and its components, Biken Journal, 1971, vol. 14, pp. 353-355.
Pastorino et al., "Epidemic Resurgence of Chikungunya Virus in Democratic Republic of the Congo"Journal of Medical Virology, 2004, vol. 74, pp. 277-282.
A. Hamdan et al., "Possible benefit of Intravenous Immunoglobulin Therapy in Lung Transplant Recipient with West Nile Virus Encephalitis" Transplant Infectious Diseases, vol. 4, No. 3, Sep. 2002, pp. 160-162.
Bayry Jagadeesh et al., "Intravenous immunoglobulin for infectious diseases: tailor-made or universal?" The Journal of Infectious Diseases, Nov. 15, 2003, vol. 188, No. 10, p. 1610.

* cited by examiner

*Primary Examiner*—Mary E Mosher
(74) *Attorney, Agent, or Firm*—24 IP Law Group; Timothy R. DeWitt

(57) ABSTRACT

The invention concerns a new medicinal product for the treatment of arboviruses, i.e.. a concentrate of immunoglobulins and F(ab)'2 and/or Fab fragments specific to said arbovirus as well as its process of preparation.

23 Claims, No Drawings

MEDICINAL CONCENTRATE OF ARBOVIRUS SPECIFIC IMMUNOGLOBULINS AND F(AB)'2 AND/OR FAB FRAGMENTS

The invention concerns a new medicinal product for the treatment of arboviruses, i.e. a concentrate of immunoglobulins and F(ab)'2 and/or Fab fragments specific to said arbovirus as well as its process of preparation.

INTRODUCTION

Viruses that employ arthropod vectors in their cycle are grouped under the general term arbovirus. Arboviruses are defined by the WHO as viruses that subsist in nature essentially or mostly through biological transmission between susceptible vertebrate hosts by hematophagous arthropods; they multiply and provoke viremia in the vertebrate, proliferate in the tissues of the arthropod and are transmitted to another vertebrate by the biting insect after an extrinsic incubation period.

Transmission of the virus from a viremic host to an adult female mosquito takes place via the blood that is sucked out when the bite occurs. The virus multiplies inside the mosquito, crosses the animal's stomach barrier and is found in the salivary glands. Contamination of a healthy human is achieved by the anticoagulant saliva of the mosquito, released just before the bite into a blood vessel. The window during which a person is a viremic host before falling ill is only a few days.

Known arboviruses belong to five virus families:
Togaviridae, genus *Alphavirus*, 28 viruses, including the viruses Chikungunya, O'Nyong Nyong, Ross River, Sindbis and Mayaro
Flaviviridae, genus *Flavivirus*, 68 viruses, including the virus of yellow fever, dengue fevers, Japanese encephalitis, the West Nile virus, tick-borne encephalitis viruses of temperate Eurasia, and the viruses that cause Kyasanur forest disease and Omsk hemorrhagic fever
Bunyaviridae, genus *Bunyavirus* (138 viruses, including the Bunyamwera virus), genus *Phleboviris* (43 viruses, including the Rift Valley Fever virus), genus *Nairovirus* (24 viruses, including the Crimea-Congo hemorrhagic fever virus)+41 unclassified viruses
Reoviridae, genus *Orbivirus* (69 viruses) and genus *Coltivirus* (2 viruses)+6 unclassified viruses
Rhabdoviridae, genus *Vesiculoviris* (18 virus) and genus *Lyssavirus* (16 viruses)+36 unclassified viruses.

The main arboviroses observed in the tropics are detailed below.

Dengues are spread over all tropical and subtropical zones of the world and represent the primary public health problem posed by arboviruses. There are four viral serotypes, called "Dengue 1, 2, 3 and 4," which do not produce cross-protection. Clinically, several forms of dengue are distinguished: asymptomatic dengue, classic dengue (CD) and the serious forms, particularly the hemorrhagic forms, hemorrhagic dengue (HD) and dengue shock syndrome (DSS), which can cause death, especially in children. All 4 types of dengue virus can be responsible for CD as well as HD. The pathophysiological mechanisms involved in the genesis of HD are unknown. The most commonly used theory refers to the phenomenon of "immunological facilitation": since a subject who has been infected with one of the four serotypes is not protected against the three others, a secondary heterologous infection could lead to HD. The vectors are mosquitoes of the genus Aedes: *Aedes aegypti* is the major vector, and *Aedes albopictus* plays an important role in rural and peri-urban areas, and is well adapted to temperate climates.

The West Nile virus is currently considered to be the most widespread of flaviviruses after the dengue virus; it affects humans either sporadically or in an epidemic manner. It has recently been illustrated emerging for the first time on the American continent, in an epidemic that occurred in New York in 1999 (62 cases, including 7 deaths). It then spread considerably in the United States, affecting over 9000 people in 44 states in 2003, including 2866 cases of encephalitis and 264 deaths. The virus had previously been found in various regions of the world, in Africa, the Middle East, India and Europe. Mosquitoes are the primary vectors of West Nile virus, mainly those of the genus *Culex*. The main hosts of the virus are birds, both wild and domestic (ducks, pigeons, etc.). They play a key role in the spread of the virus. The West Nile virus infects humans mainly via the route of a vector mosquito. The infection is characterized by the sudden onset of a high fever after 3 to 6 days of incubation. This fever is accompanied by headaches and back pain, muscle pain, coughing, swelling of neck lymph nodes and often skin rash, nausea, abdominal pain, diarrhea and respiratory symptoms. In under 15% of cases, complications arise: meningitis, encephalitis, and rarely hepatitis, pancreatitis or myocarditis. Generally, the patient recovers spontaneously, sometimes with sequelae. However, the disease can be deadly in seniors and sometimes in young children.

Yellow fever (YF) continues to be a formidable endemic and a constant threat in Subsaharan Africa and tropical America. It is due to the amaril virus. It manifests in the form of a hemorrhaging hepatonephritis, amaril typhus, with a starting or "red" phase, remission on the $3^{rd}$ day, and a stasis or "yellow" phase, with jaundice, vomiting, hemorrhaging (mainly in the GI tract), and renal syndrome. The epidemiology is complex in that, in natural areas, the amaril virus circulates continually among monkey populations, due to wild simiophilic mosquitoes that act as vectors. It was only by accident, when humans came into contact with such a jungle cycle, that the first human cases occurred.

Chikungunya (abbreviated CHIK) is transmitted by mosquitoes of the genus *Aedes*. The name comes from the Bantu language, and means: he who bends, he who curls up, or bent man's disease because it induces very severe joint pain combined with stiffness, which gives infected patients a very characteristic bent appearance.

Out of over 950 species of mosquitoes, several of them are able to transmit chikungunya, but only *Aedes aegypti* and *Aedes albopictus* have been identified to date as epidemic vectors, due to their adaptation to areas of human habitation. These same species are also involved in the transmission of other arboviruses: dengue, hemorrhagic dengue fever (HDP), yellow fever, etc.

The clinical profile is dominated by a high fever similar to that of dengue (dengue is often mistaken for chikungunya and vice-versa), combined with incapacitating joint pain and sometimes skin rash. However, there are severe forms that have been ignored up to now: fulminating hepatitis, heart attacks, meningoencephalitis, etc. Several other arboviruses of the alphavirus genus (approximately 30-kD capsid and polyadenylated RNA at 3') such as Ross River, O'nyong-nyong and Mayaro have been associated with similar symptoms.

Incubation of the disease lasts from four to seven days on average. Viremia, the presence of the virus in the blood and therefore of possible transmission, extends over approximately five days. Antibodies then develop. They remain in the blood. Immunity is therefore usually acquired for life.

A vaccine is available to prevent yellow fever. Vaccination is systematic in exposed populations. However, 60 to 80% of the population must be immunized (naturally or through vaccination) to avoid epidemics. Antibodies appear after about ten days. Vaccination is contraindicated in pregnant women and infants younger than 6 months.

A vaccine is also in use in Europe against tick-borne encephalitis. It is sold under the name TICOVAC® (Baxter SA).

A phase I and a phase II study have been conducted in the United States for a chikungunya vaccine by the United States Army Medical Research Institute of Infectious Diseases (Edelman R et al. "Phase II safety and immunogenicity study of live chikungunya virus vaccine" TSI-GSD-218. Juin 2000; Am J Trop Med Hyg, 62:681-5).

There is currently no virucidal treatment for arboviruses.

Treatment is purely symptomatic, to lower the fever and reduce pain.

PRIOR ART

Several studies have demonstrated the efficacy of immunoglobulin injections containing anti-hepatitis A antibodies in subjects at risk of being exposed to this virus, before the development of the hepatitis A vaccine (Ohara et al., Jpn J Exp Med, 1986 October; 56(5):229-33; Conrad M E et al., J Infect Dis, 1987 July; 156(1):56-63).

The specific immunoglobulins of hepatitis B, or anti-HBs, are widely used to protect any non-vaccinated person who receives a cut with a contaminated article, newborns of mothers who are HBs antigen positive (in this case, injection must be performed immediately after birth and must be accompanied by initiation of vaccination), liver transplant patients to avoid reinfection of the graft, and sexual partners of subjects who are HBs antigen positive while waiting for the vaccination to take effect. These immunoglobulins allow the setting up of a protection, either before exposure to the risk or during the 24 hours following contact with the infection (accidental prick).

SUMMARY OF THE INVENTION

Faced with this absence of an established virucidal treatment and only one vaccine having received marketing authorization, the Applicant has sought to develop a medicinal product to treat or prevent arboviroses, based on specific immunoglobulins that make it possible to quickly immunize exposed people.

The Applicant has demonstrated in a surprising manner that such a treatment requires the combination of immunoglobulins and F(ab')2 and/or Fab fragments specific to the arbovirus to be treated in order to be effective.

DEFINITIONS

The term "concentrate" refers to a product obtained by elimination of certain components. A concentrate of immunoglobulins is obtained by elimination of certain components of the plasma to achieve an immunoglobulin-enriched plasma fraction.

The term "immunoglobulin" (Ig) refers to a natural globulin, present mainly in the plasma, with antibody functions, which can be used in curative or preventive therapy.

Immunoglobulins are heterodimers composed of 2 heavy chains and 2 light chains, linked by disulfide bridges. Each chain is constituted in N-terminal position of a variable domain or region (coded for by rearranged V-J genes for the light chain and V-D-J for the heavy chain) that is specific to the antigen against which the antibody is directed, and in C-terminal position, of a constant region, composed of a single CL domain for the light chain or 3 domains (CH1, CH2 and CH3) for the heavy chain. The combination of variable domains and CH1 and CL domains of the heavy and light chains forms the Fab parts, which are connected to the Fc region by a very flexible hinge region that allows each Fab to bind to its antigen target while the Fc region, which mediates the effector properties of the antibody, remains accessible to effector molecules such as FcγR receptors and C1q.

IgG are the most common immunoglobulins (75 to 80% of circulating antibodies). They protect the body against bacteria, viruses and toxins that circulate in the blood and the lymph. In addition, they quickly bind to the complement (one of the components of the immune system). They also participate in memory response, which is the basis of immunity upon which the mechanism of vaccination is founded. Lastly, immunoglobulins G cross the placental barrier and thus produce passive immunity in the fetus.

IgA are mainly found in secretions such as saliva, intestinal juices, sweat and breast milk. The main role of immunoglobulins A is to prevent pathogenic agents from binding to cells, particularly to the protective cells that make up the mucous membranes and epidermis.

IgM are immunoglobulins secreted upon the body's first contact with an antigen. They are the first type of immunoglobulins released by plasmocytes. The presence of IgM in the blood indicates a current infection.

Enzymatic proteolysis of immunoglobulins by papain generates 2 identical fragments, which are known as Fab fragment (Fragment Antigen Binding), and one Fc (crystallizable fraction) fragment. The Fc fragment supports the effector functions of immunoglobulins.

By pepsin proteolysis, an F(ab')2 fragment is generated, in which the two Fab fragments remain linked by two disulfide bridges, and the Fc fragment is split into several peptides. The F(ab')2 fragment is formed from two Fab' fragments (one Fab' fragment consisting of one Fab and a hinge region), linked by intercatenary disulfide bridges to form an F(ab')2.

The term "chromatography" refers to a method of separation of the components of a mixture based on their selective retention, using a suitable medium.

DETAILED DESCRIPTION OF THE INVENTION

First of all, the invention relates to a concentrate of immunoglobulins and F(ab)'2 and/or Fab fragments specific to an arbovirus, as a medicinal product.

The use of immunoglobulin-enriched human plasma fractions for the treatment of various infections or congenital deficiencies has been known since the development of the ethanol precipitation process by Cohn (Cohn et al. 1946, J. Am. Chem. Soc. 68, 459; Oncley et al. 1949, J. Am. Chem. Soc. 71, 541).

Such F(ab)'2 or Fab fragments, which contain the antibody's binding site, may have lost a certain number of properties of the whole antibody from which they were derived, such as the ability to bind to Fcgamma receptors.

The arbovirus in question, able to be treated with a concentrate as set forth in the invention, may be, for example, one of the dengue viruses, the yellow fever virus, the West Nile virus, the chikungunya virus, the Ross River virus, the O'nyong-nyong virus or the Mayaro virus.

In the concentrate according to the invention, all of the combinations are possible between a mixture of immunoglobulins A, G and/or M and F(ab)'2 and/or Fab fragments of Ig A, G and/or M specific to an arbovirus.

In particular, the concentrate according to the invention is a concentrate of immunoglobulins A, G, and M and F(ab)'2 and/or Fab fragments specific to an arbovirus.

Preferably, the concentrate according to the invention is a concentrate of immunoglobulins G exclusively or a concentrate of immunoglobulins M exclusively, and of F(ab)'2 and/or Fab fragments specific to an arbovirus.

Particularly preferably, the concentrate according to the invention is made up of a concentrate of immunoglobulins G exclusively and of F(ab)'2 and/or Fab fragments of IgG and IgM specific to an arbovirus.

Preferably, the concentrate according to the invention contains at least 50% of IgG immunoglobulins, and from 90 to 98% of proteins which react with antibodies specifically directed against human immunoglobulins, particularly from 5 to 50% F(ab)'2 and/or Fab, particularly at least 50 to 60 g/L of Ig and fragments for a pharmaceutical preparation.

According to the invention, from 1 to 10 mmol of magnesium and/or zinc could be added to the concentrate.

Another subject of the invention consists in the use of a concentrate according to the invention for the manufacturing of a medicinal product for the treatment of said arbovirus.

This treatment is prophylactic and/or curative. It is used either to confer passive immunity to persons not yet infected in a region of epidemic, or to care for patients already infected with the virus.

The medicinal product in question is administered by topical, oral, mucosal, intramuscular or intravenous route.

It is effective for several weeks, approximately 21 days, beyond which period this administration must be repeated if the epidemic or symptoms persist.

The invention also concerns a process for preparing a concentrate according to the invention.

This process consists of mixing a concentrate of immunoglobulins specific to an arbovirus and a concentrate of immunoglobulins specific to the same arbovirus that have undergone proteolysis in order to obtain F(ab)'2 and Fab fragments specific to this arbovirus. This process therefore requires the preparation of at least one concentrate of immunoglobulins.

This process begins with the creation of a pool of at least 1000 plasma donations, each donation containing a sufficient titer of Ig directed against said arbovirus. A serum containing a sufficient titer corresponds, for example, to a serum which remains positive for detection of anti-chikungunya antibodies, after being diluted to $1/1000$, when titer is measured by a method such as Elisa.

These donations come from people who have been in contact with the disease, or patients who have developed the disease.

Titration can be performed according to C. van de Water et al., Journal of Immunological Methods, 166 (1993), 157-164.

In order to enrich this plasma pool in immunoglobulins, the other components of the plasma, known as "lipid and protein contaminants" are precipitated in a single step. This purification by precipitation in a single step may take place by diluting the plasma in precipitation conditions according to Steinbuch (Steinbuch M., Archiv. Biochem. Biophys., 134, 279-284) and by adding caprylic acid. It can also be obtained through addition of precipitation agents such as, for example, Rivanol, aluminum chloride, cetylpyridinium chloride, octanoic acid, polyphosphates and in the presence of adsorption agents such as, for example, tricalcium phosphate and bentonite.

The supernatant resulting from precipitation can constitute the concentrate of immunoglobulins. It therefore contains a mixture of IgG, A and M. This supernatant is recovered, for example by filtration, optionally by adding at least one filtration additive.

The supernatant resulting from centrifugation or filtration can undergo viral deactivation processing such as, for example, a conventional viral deactivation processing with a solvent/detergent (Triton X100).

If the precipitation carried out was a "caprylic" type precipitation, such as described above, the residues of caprylic acid in the supernatant are eliminated by PO4 calcium.

In order to obtain a concentrate of IgG, IgA or IgM, the teachings described in the patent EP1385886 can be applied, in particular methods relating to pH adjustment, adsorption on a pre-loaded column, adsorption on the column of the supernatant containing the immunoglobulins and accompanying proteins, column washing and sequential elution of the various immunoglobulins categories, e.g. IgG, IgA, or IgM. After the viral deactivation step, the supernatant then undergoes an additional step of purification by chromatography on an anion exchanger performed in alkaline pH. In particular, the pH of the supernatant is adjusted beforehand to a pH from 8.9 to 9.1, and the column is loaded with a buffer at a pH from 8.9 to 9.1. The chromatography step allows adsorption of immunoglobulins on the column and passage of non-retained proteins into the effluent. Chromatography can be performed, for example, on a reticulated polysaccharide or vinyl polymer gel, grafted with DEAE, TMAE or QAE groups.

After washing the column with the same buffer as the loading buffer to eliminate non-retained proteins, immunoglobulins G are eluted with a phosphate buffer, the pH of which is from 4 to 7, preferably at pH 6.2.

An optional subsequent elution with the same phosphate buffer supplemented with 100 to 175 mM NaCl, preferably 150 mM, at a pH ranging from 6 to 6.3, can be used to collect IgA.

An optional subsequent elution with the same buffer adjusted to a pH ranging from 6 to 7 and supplemented with 250 to 350 mM NaCl, preferably 300 mM, can be used to collect IgM.

Any type of mixture between IgA, IgG and IgM can be considered by mixing the concentrates as they are described above.

Immunoglobulins thus eluted and collected can be concentrated by ultrafiltration and put, for example, through conventional sterilizing filtration then filtration through nanometric filters with porosity decreasing from 100 to 15 nanometers.

To the solution of concentrated and filtered immunoglobulins is added a pharmaceutically acceptable stabilzer agent, such as those described in the patent application WO2004/091656, then this solution is packaged as a sterile solution and optionally frozen and/or lyophilized.

Application of nanofiltration makes it possible to eliminate viruses that are resistant to viral deactivation solvent/detergent treatment.

A part of the concentrate of immunoglobulins thus obtained, or another concentrate of immunoglobulins obtained in the manner described above, is subjected to proteolysis to obtain F(ab)'2 or Fab fragments. Concentrate of Ig and mixture of fragments resulting from proteolysis are then mixed.

Thus, a concentrate of IgG and F(ab)'2 and/or Fab of IgG and IgM is obtained, by:
(1) preparing a concentrate of IgG as described above,
(2) preparing a concentrate of IgM as described above,
(3) mixing and digesting a part of the IgG concentrate and a part of the IgM concentrate to obtain a mixture of F(ab)'2 and/or Fab fragments of IgG and IgM,
(4) Mixing (1) and (3).

In order to obtain F(ab)'2 fragments, proteolysis is performed at pH 4.0, at 35° C., with 1% pepsin, this percentage corresponding to the weight ratio of pepsin to total weight of protein weight of the concentrate (IGLOO protocol).

To obtain Fab fragments, proteolysis is performed with 1% papain, this percentage corresponding to the weight ratio of papain to total weight of protein weight of the concentrate.

Proteolysis of immunoglobulins G, A and/or M can also be performed by using plasmin and/or trypsin, the implementation of these proteases being well known by the person skilled in the art.

The example disclosed below describes a particular embodiment of the invention but should not be considered as limiting the scope thereof.

EXAMPLE 1

Preparation of an Anti-Chikungunya Immunoglobulin Concentrate 1-1. Creation of a Plasma Pool One litre of plasma rich in anti-chikungunya antibodies is collected from volunteer donors who were recently infected by chikungunya virus and cured from disease symptoms. Antibody titer is measured by Elisa, and consisted in fixing virus antigens on a microtitration plate, then revealing specific antibodies through a horse radish peroxydase labelled reagent directed against immunoglobulins. For creation of the plasma pool, positively assayed samples at a dilution of at least 1/1000 in the context of a "specific" Elisa method are retained.

1-2. Preparation of Immunoglobulins

Plasma pool resulting from step 1-1 is cooled to −3° C. and, during cooling, ethanol is added in a volume sufficient to obtain a final ethanol concentration of 8%. The precipitate formed thereby is discarded.

The pH of the supernatant is then adjusted to pH 5.9, through addition of acetate buffer, for example, cooled to −5° C., and completed with a volume of ethanol which is sufficient to obtain a final ethanol concentration of 19%. The precipitate formed thereby is collected by centrifugation, for example, and resuspended in acetate buffer, for example, to obtain a final pH from 4.7 to 4.9.

Octanoic acid is then added at 20° C., under vigorous stirring, to obtain a final octanoic acid concentration of 20 g/l.

The precipitate formed thereby is separated by centrifugation or alluvial filtration and discarded. Tricalcium phosphate or activated carbon are added to the supernatant, then the mixture is clarified by deep-bed filtration.

The pH of immunoglobulin containing supernatant, which results from the clarification step, is adjusted to pH 9 through addition of NaOH/glycine buffer, for example, and supernatant is applied to an anion exchange column (Fractogel TMAE, for example), which is loaded at pH 9 with a glycine/NaCl buffer at pH 9.

Washing with loading buffer is performed until the column exit OD at 280 nm is closed to the $OD_{280}$ measured upon establishment of the basal line.

IgG elution is then performed with a first sodium phosphate buffer at pH 6.2. A second elution is performed with a phosphate buffer supplemented with NaCl 300 mM.

The corresponding eluate contains IgA, IgM and part of IgG4. The detailed operating process of this purification is disclosed in EP 1385886.

1-3. Preparation of an Active Concentrate Against Chikungunya

25% of the first eluate, containing the IgG, are withdrawn and added to eluates containing IgG4, IgA and IgM. This immunoglobulin mixture is concentrated to 50 g/l through ultrafiltration on a membrane, the cutoff threshold of which is equal to or lower than 30 kD.

The pH of the concentrated mix is adjusted by diafiltration against a citrate buffer at pH 3.8 to 4.2, to obtain an acidic pH comprised in this range. The solution is supplemented with pepsin (10000 FIP/mg) such that the amount of pepsin accounts for 1% of the total amount of proteins contained in the concentrated mixture. This solution is then filtered under sterile conditions at 0.2 μm and incubated 20 h at 37° C.

After incubation, protein hydrolysate is neutralized, for example, by adding sodium hydroxide at pH 6.2+/−0.2. Neutralized protein hydrolysate is diafiltrated against a glycine buffer at pH 6.2+/−0.2, until $OD_{280}$ is about 0.005, with $OD_{280}$ being measured on the filtrate line of the 30 kD cutoff threshold membrane.

Peptides resulting from pepsin proteolysis, the size of which is equal to or lower than 30 kD are discarded upon passage through the cutoff threshold membrane. The obtained protein hydrolysate therefore contains Fab fragments, F(ab)'2 fragments but lacks Fc fragments.

The resulting protein hydrolysate in then mixed with the remaining 75% of the first eluate, which contains the IgG. The mix is subsequently concentrated by ultrafiltration to reach a final concentration ranging from 50 to 160 g/l, depending on the selected route of administration. The titer of the concentrate is measured according to the method described in Edelman, R et al. (American Journal of Tropical Medicine and Hygiene, 62 (6), 2000, pages 681-685). The thus obtained titer in anti-chikungunya specific antibodies of the concentrate is at least 3 to 10 times above that of starting plasma.

1-4. Use of the Preparation

The concentrate resulting from step 1.3 is stabilised by mixing with a formulation comprising pharmaceutically acceptable excipients, such as, for example, glycine under a final concentration of 0.22M, or such as those described in the patent application WO 2004/091 656. The pH of the formulation added to the concentrate is compatible with obtaining a liquid mixture, the pH of which ranges from 4.2 to 5.6.

The resulting liquid mixture may be administered, for example, by intravenous, subcutaneous or intramuscular routes, depending on the phlebological state of the receiver.

The administered dose corresponds to 0.2 to 0.8 ml/kg and may, in the case of an epidemic, be administered as a precautionary measure every 3 weeks to especially exposed patients, for example, to elderly, pregnant women or new borns.

The invention claimed is:

1. A medicinal product comprising a concentrate of immunoglobulins and F(ab)'2 and/or Fab fragments specific to an arbovirus.

2. The medicinal product according to claim 1, wherein said arbovirus is selected from the group consisting of the dengue viruses, the yellow fever virus, the West Nile virus, the chikungunya virus, the Ross River virus, the O'nyong-nyong virus, and the Mayaro virus.

3. The medicinal product according to claim 1, wherein the immunoglobulins are immunoglobulins A, G and M.

4. The medicinal product according to claim 1, wherein the immunoglobulins are immunoglobulins G.

5. The medicinal product according to claim 1, wherein the immunoglobulins are immunoglobulins M.

6. The medicinal product according to claim 1, comprising from 90 to 98% immunoglobulins and F(ab)'2 and/or Fab.

7. The medicinal product according to claim 1, comprising from 5 to 50% F(ab)'2 and/or Fab.

8. The medicinal product according to claim 1, wherein the F(ab)'2 and/or Fab fragments are F(ab)'2 and/or Fab fragments of IgG and/or IgM.

9. The medicinal product according to claim 1, further comprising from 1 to 10 mmol of magnesium.

10. The medicinal product according to claim 1, further comprising from 1 to 10 mmol of zinc.

11. A method of making a medicinal product comprising forming a concentrate of immunoglobulins and F(ab)'2 and/or Fab fragments specific to an arbovirus.

12. The method according to claim 11 wherein said medicinal product is in a form to be administered by a route selected from the group consisting of topical, subcutaneous, oral, intramuscular, intravenous.

13. A process for preparing a concentrate according to claim 1, wherein said process comprises:
    creating a pool of at least 1000 plasma donations, each donation containing a sufficient titer of Ig directed against said arbovirus,
    precipitating lipid and protein contaminants in a single step,
    recovering an Ig concentrate in the supernatant (1),
    subjecting a part of the earlier concentrate to proteolysis to obtain F(ab)'2 and/or Fab fragments (2)
    mixing fractions (1) and (2).

14. A process for preparing a concentrate according to claim 1, wherein said process comprises the following steps:
    creating a pool of at least 1000 plasma donations, each donation comprising a sufficient titer of anti-chikungunya Ig.
    precipitating lipid and protein contaminants in a single step,
    chromatographing the supernatant on an anion exchanger in alkaline pH,
    eluting IgG by a phosphate buffer at a pH between 4 and 7 to obtain an IgG concentrate (1),
    optionally, subsequently eluting IgA with the same phosphate buffer further comprising 100 to 175 mM NaCl, preferably 150 mM, at a pH of 6 to 6.3 (1),
    optionally, subsequently eluting IgM with the same phosphate buffer further comprising 250 to 350 mM NaCl at a pH between 6 and 7 (1),
    optionally, mixing IgG, IgA and IgM concentrates (1),
    subjecting a part of the earlier concentrate to proteolysis to obtain F(ab)'2 and/or Fab fragments (2),
    mixing fraction (1) and fraction (2).

15. The process according to claim 14, wherein the pH of the supernatant is adjusted to between 8.9 and 9.1 and the chromatography column is loaded with a buffer at a pH 8.9 to 9.1 before chromatography.

16. A process for preparing a concentrate of immunoglobulins and F(ab)'2 and/or Fab fragments specific to an arbovirus, wherein said process comprises:
    (1) preparing a concentrate of IgG according to claim 14,
    (2) preparing a concentrate of IgM according to claim 14,
    (3) mixing and subjecting a part of the IgG concentrate and a part of the IgM concentrate to proteolysis to obtain a mixture of F(ab)'2 and/or Fab fragments of IgG and IgM,
    (4) mixing (1) and (3).

17. The process according to claim 13, wherein proteolysis to obtain F(ab)'2 fragments takes place in pepsin 1% by weight of proteins at pH 4 and 35° C.

18. The process according to claim 13, wherein the proteolysis to obtain Fab fragments takes place in papain.

19. The process according to claim 13, wherein the precipitation is a caprylic precipitation, and wherein residues of caprylic acid in the supernatant are eliminated by PO4 calcium.

20. The process according to claim 13, wherein the precipitate is separated by filtration after addition of at least one filtration additive.

21. The process according to claim 13, wherein the supernatant is treated with a solvent/detergent.

22. The process according to claim 13, wherein the eluted immunoglobulins are concentrated by ultrafiltration and put through conventional sterilizing filtration then filtration through nanometric filters with porosity decreasing from 100 to 15 nanometers.

23. The process according to claim 13, wherein a pharmaceutically acceptable stabilizer is added to the solution of concentrated and filtered immunoglobulins, then it is packaged as a sterile solution and optionally frozen and lyophilized.

* * * * *